United States Patent
Zhang et al.

(10) Patent No.: US 10,500,568 B2
(45) Date of Patent: Dec. 10, 2019

(54) CORE-SHELL STRUCTURE SUPPORTED TUNGSTEN COMPOSITE CATALYST AND PREPARATION METHOD AND USE THEREOF

(71) Applicants: Hangzhou Normal University, Zhejiang (CN); Zhejiang Benli Technology Co., Ltd., Taizhou, Zhejiang (CN)

(72) Inventors: Pengfei Zhang, Zhejiang (CN); Chao Shen, Zhejiang (CN); Xiaoling Li, Zhejiang (CN); Jun Xu, Zhejiang (CN); Haining Gu, Zhejiang (CN)

(73) Assignees: Hangzhou Normal University, Zhejiang (CN); Zhejiang Benli Technology Co., Ltd., Taizhou, Zhejiang (CN)

( * ) Notice: Subject to any disclaimer, the term of this patent is extended or adjusted under 35 U.S.C. 154(b) by 73 days.

(21) Appl. No.: 15/848,821

(22) Filed: Dec. 20, 2017

(65) Prior Publication Data

US 2019/0009255 A1  Jan. 10, 2019

(30) Foreign Application Priority Data

Jul. 5, 2017  (CN) .......................... 2017 1 0540001

(51) Int. Cl.

| | | |
|---|---|---|
| *C07D 215/00* | (2006.01) | |
| *B01J 23/00* | (2006.01) | |
| *B01J 35/00* | (2006.01) | |
| *B01J 37/00* | (2006.01) | |
| *B01J 23/888* | (2006.01) | |
| *C07D 215/56* | (2006.01) | |
| *B01J 37/34* | (2006.01) | |

(52) U.S. Cl.
CPC ........... *B01J 23/888* (2013.01); *B01J 35/008* (2013.01); *B01J 35/0033* (2013.01); *C07D 215/56* (2013.01); *B01J 37/342* (2013.01); *B01J 2523/00* (2013.01); *B01J 2523/41* (2013.01); *B01J 2523/69* (2013.01); *B01J 2523/842* (2013.01); *Y02P 20/584* (2015.11)

(58) Field of Classification Search
CPC ... C07D 215/56; B01J 23/888; B01J 35/0033; B01J 37/342
See application file for complete search history.

(56) References Cited

FOREIGN PATENT DOCUMENTS

| CN | 101020658 | * | 8/2007 | ........... C07D 215/56 |
|---|---|---|---|---|
| CN | 101838238 | * | 9/2010 | ........... C07D 215/56 |
| CN | 107175131 | * | 9/2017 | .............. B01J 23/18 |

* cited by examiner

*Primary Examiner* — Sikarl A Witherspoon
(74) *Attorney, Agent, or Firm* — Muncy, Geissler, Olds & Lowe, P.C.

(57) ABSTRACT

The present invention discloses a core-shell structure supported tungsten composite catalyst and a preparation method and use thereof. Most of the existing synthesis methods of the main ring of quinolone drugs have the defects of many synthesis steps, cumbersome operation, large amount of three wastes, higher costs and the like. The present invention prepares a magnetic separable core-shell supported tungsten composite catalyst, $WO_3/SiO_2/Fe_3O_4$, by preparing $Fe_3O_4$ colloid and $SiO_2/Fe_3O_4$ composite nano-particles. This magnetic separable core-shell supported tungsten composite catalyst, $WO_3/SiO_2/Fe_3O_4$, is used to catalyze and synthesize quinolone compounds. The present invention provides an efficient preparation method of quinolone compounds using a catalyst which can be recovered by magnetic separation and recycled. The catalyst prepared by the present invention can be reused in the preparation of quinolone compounds and still retains the original activity without deactivation, which not only greatly improves the production efficiency, but also reduces the environmental pollution.

19 Claims, 1 Drawing Sheet

CORE-SHELL STRUCTURE SUPPORTED TUNGSTEN COMPOSITE CATALYST AND PREPARATION METHOD AND USE THEREOF

TECHNICAL FIELD

The present invention relates to a catalyst, a preparation method and use thereof, in particular to a magnetic separable core-shell structure supported tungsten composite catalyst, a preparation method thereof and use in the synthesis of quinolone compounds.

BACKGROUND ART

Quinolone antimicrobials are one of the most widely used anti-infectives in clinic. As quinolone drugs have the advantages of wide antimicrobial spectrum, strong antimicrobial activity, convenient administration, small adverse reactions, no cross-resistance with other antibiotics and the like, they have become the first choice for clinical drug combination and have a large market demand.

In recent years, studies have found that quinolone drugs have new efficacies on various diseases such as malaria, AIDS and tumors. Quinolone compounds also have good activity on prokaryotic type II topoisomerase, gyrase and DNA topoisomerase IV. Moreover, the activity spectrum and range of application are constantly expanding.

However, the synthesis of the main ring of quinolone drugs goes substantially through three steps in order to obtain its key intermediate, which is then subjected to hydrolysis and substitution reactions to yield quinolone drugs. The synthesis has the defects of many steps, cumbersome operation, large amount of three wastes, higher costs and the like. Therefore, looking for new synthesis techniques and exploring new catalyst preparation methods are the focuses of current researches. The following formula (I) is the structure of quinolone molecules.

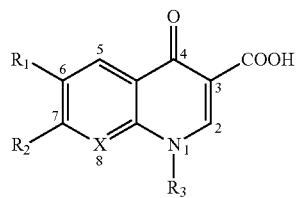

(I)

SUMMARY OF THE INVENTION

One of the objects of the present invention is to provide a preparation method of a magnetic separable core-shell structure supported tungsten composite catalyst. When the magnetic separable core-shell structure supported tungsten composite catalyst prepared by the present method is used in the synthesis of quinolone compounds, the production costs are reduced, the three wastes are reduced and the product quality is improved.

To this end, the technical solution adopted by the present invention is: a preparation method of a core-shell structure supported tungsten composite catalyst, comprising the steps of:

step 1), adding a reducing agent and a base into an aqueous solution of iron compound, heating to 50-80° C. and stirring to obtain $Fe_3O_4$ colloid;

step 2), adding the $Fe_3O_4$ colloid obtained in the step 1), tetraethyl orthosilicate and a hydrolysis catalyst into an appropriate amount of dispersion solvent and allowing to react for 4-8 hours to obtain $SiO_2/Fe_3O_4$ composite nano-particles; and step 3), adding the $SiO_2/Fe_3O_4$ composite nano-particles obtained in step 2) into an aqueous solution of ammonium metatungstate, stirring for 8-14 hours and drying at 90-150° C. to obtain a first solid, which is calcined at 450-650° C. for 1-6 hours to obtain a magnetic separable core-shell structure supported tungsten composite catalyst, $WO_3/SiO_2/Fe_3O_4$;

wherein the molar ratio above of the iron compound: tetraethyl orthosilicate:ammonium metatungstate=1:1-10: 0.1-1;

and wherein the iron compound is $FeCl_3$, $FeCl_3 \cdot 6H_2O$ or ferric triacetylacetonate; the reducing agent is $Na_2SO_3$, ascorbic acid or hydrazine hydrate; and the base is aqueous ammonia, sodium hydroxide or sodium acetate.

As a preferred embodiment of the above technical solution, the iron compound is $FeCl_3$.

As a preferred embodiment of the above technical solution, the reducing agent is $Na_2SO_3$.

As a preferred embodiment of the above technical solution, the base is aqueous ammonia.

As a preferred embodiment of the above technical solution, in step 1), after heating, polyvinylpyrrolidone is added as a surfactant, the mixture is stirred continuously, then centrifuged and washed with water, and finally dispersed and water is then removed to obtain $Fe_3O_4$ colloid.

As a preferred embodiment of the above technical solution, in step 2), the dispersion solvent is ethanol, and the hydrolysis catalyst is aqueous ammonia.

As a preferred embodiment of the above technical solution, in step 3), the first solid is first ground through a 120-mesh standard sieve and then calcined at 450-650° C. for 1-6 hours.

Another object of the present invention is to provide a magnetic separable core-shell structure supported tungsten composite catalyst, $WO_3/SiO_2/Fe_3O_4$, obtained by the above preparation method.

Yet another object of the present invention is to provide use of the above magnetic separable core-shell structure supported tungsten composite catalyst, $WO_3/SiO_2/Fe_3O_4$, in the synthesis of quinolone compounds, wherein the reaction steps are as follows:

step 1), stirring and mixing ethyl formylacetate sodium salt, a non-polar organic solvent and the $WO_3/SiO_2/Fe_3O_4$ catalyst, introducing an amine compound, adding 2,4-dichloro-5-fluorobenzoyl chloride and allowing to react for 0.5-3 hours;

step 2), following step 1), adding a primary amine dropwise while introducing $CO_2$ to control the reaction pressure at 1-5 atmospheres and allowing to react for 0.5-3 hours;

step 3), following step 2), adding an alkali metal hydroxide and a non-polar organic solvent, stirring and raising the temperature to 100° C. for half an hour, filtering to recover the catalyst and increasing the pressure to recover the non-polar organic solvent; and step 4), following step 3), adding an appropriate amount of water, raising the temperature to 100° C., adding hydrochloric acid dropwise to adjust the power of hydrogen to control the pH range at 4.8-6.5, precipitating crystals, followed by centrifugation and drying, and obtaining quinolone compounds;

wherein the non-polar organic solvent is toluene, xylene or a mixture of the former two; the amine compound is dimethylamine, diethylamine or dicyclohexylamine; the primary amine is cyclopropylamine or S-propylene glycol amine; and the alkali metal hydroxide is sodium hydroxide, lithium hydroxide or potassium hydroxide.

The synthesis method of the key intermediate of quinolone drugs of the present invention uses an ethyl formylacetate, cyclopropylamine and the like as the main starting materials, which are subjected to an "one-pot" reaction with a polyhalogenated aroyl chloride under the catalysis of a novel magnetic separable core-shell supported tungsten composite catalyst, $WO_3/SiO_2/Fe_3O_4$, to prepare the main ring compound of quinolones.

As a preferred embodiment of the above technical solution, the non-polar organic solvent is toluene, the amine compound is dimethylamine, the primary amine is cyclopropylamine, and the alkali metal hydroxide is sodium hydroxide.

The preparation process of quinolone compounds is as follows:

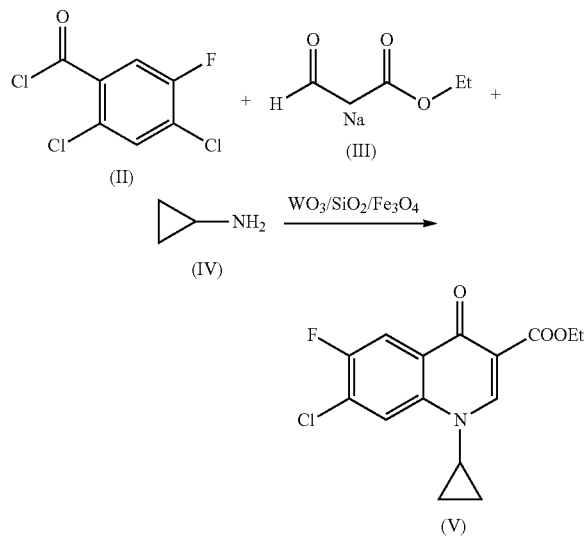

The present invention has the following advantages. The present invention prepares a magnetic separable core-shell supported tungsten composite catalyst, $WO_3/SiO_2/Fe_3O_4$, which is used to catalyze and synthesize quinolone compounds and is recovered by way of magnetic separation. Compared with the traditional use of strong base catalysts, the coupling efficiency to sulfur through C—N coupling is significantly improved, the reaction time is shortened, and the the process cost is significantly reduced. At the same time, the present invention provides an efficient preparation method of quinolone compounds using a catalyst which can be recovered by magnetic separation and recycled. The catalyst prepared by the present invention can be reused in the preparation of quinolone compounds and still retains the original activity without deactivation, which not only greatly improves the production efficiency, but also reduces the environmental pollution. Compared with the traditional processes, the preparation method of quinolone compounds of the present invention has the advantages of simple operation, high production efficiency, less dosage of strong base, low production cost and the like, and is an efficient, economical and environmentally friendly production process.

Figure 1:
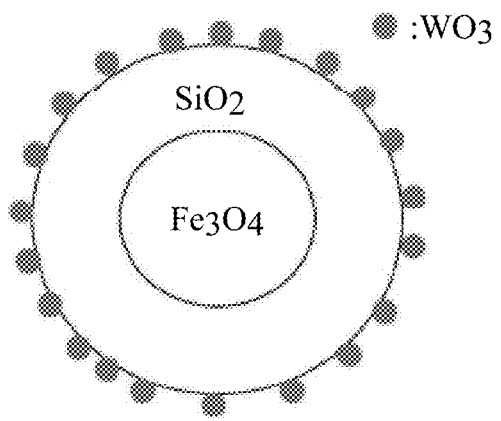
FIG. 1 is a schematic structural view of the magnetic separable core-shell supported tungsten composite catalyst, $WO_3/SiO_2/Fe_3O_4$, of the present invention.
Figure 2:
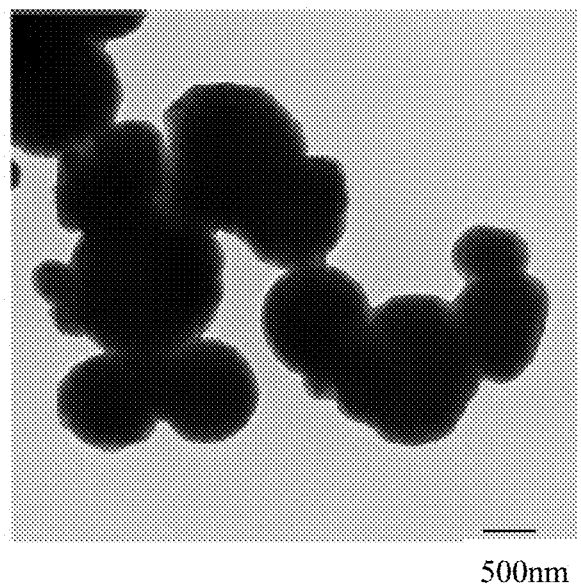
FIG. 2 is a transmission electron micrograph (TEM) of the core-shell catalyst of Example 5 of the present invention.

It can be seen from FIG. 2 that the prepared catalyst has the characteristics of uniform coating, small particle size, less agglomeration and the like, which helps to efficiently catalyze a cyclization reaction.

DETAILED DESCRIPTION OF EMBODIMENTS

The present invention will be further described with reference to the following examples, but the protection scope of the present invention is not limited thereto. The preparation process of the magnetic separable core-shell supported tungsten composite catalyst, $WO_3/SiO_2/Fe_3O_4$, of the present invention is as follows:

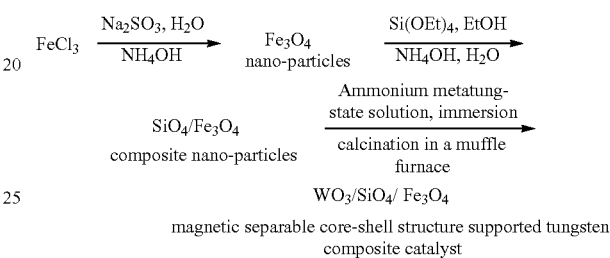

Firstly, $Fe_3O_4$ nano-particles are prepared by partial reduction-coprecipitation method; then, $SiO_2/Fe_3O_4$ composite nano-particles are prepared by sol-gel method; and finally, the magnetic separable core-shell supported tungsten composite catalyst, $WO_3/SiO_2/Fe_3O_4$, is prepared by immersion calcination method.

Examples 1-12

The preparation method for preparing the magnetic separable core-shell supported tungsten composite catalyst, $WO_3/SiO_2/Fe_3O_4$, was carried out sequentially through the following steps.

1). Preparation of $Fe_3O_4$ nano-particles $Fe_3O_4$ nano-particles were prepared by partial reduction-coprecipitation method. At room temperature, 16.3 g of $FeCl_3$ was added into a 250 mL flask and dissolved with water. Under the protection of nitrogen, a reducing agent, $Na_2SO_3$ solution (containing 2.7 g of $Na_2SO_3$), was added slowly and stirred. After 10 minutes, 40.8 mL of aqueous ammonia with a mass fraction of 28% was added rapidly, at which time the formation of black particles was observed. The temperature of the thermostatic water bath was raised to 70° C., 2 mL of oleylamine was added as a surfactant and stirring was continued for 6 hours. Afterwards, the product was centrifuged and washed several times with deionized water, and finally dispersed and then deionized water was removed to obtain stable $Fe_3O_4$ colloid.

2). Preparation of $SiO_2/Fe_3O_4$ composite nano-particles

At ambient temperature, 10 mL of EtOH, 1.16 g of $Fe_3O_4$ colloid, 8 mL of deionized water and 12.5 g of TEOS (tetraethyl orthosilicate) were added sequentially into a 100 mL beaker, stirring was continued for 30 minutes, followed by the addition of 42 mL of aqueous ammonia with a mass fraction of 28% to catalyze the hydrolysis and condensation of TEOS (tetraethyl orthosilicate). After the reaction was carried out for 6 hours under a sealed state, the product was separated by centrifugation, and washed respectively with EtOH and deionized water several times to obtain $SiO_2/Fe_3O_4$ composite nano-particles.

3). Preparation of magnetic separable core-shell supported tungsten composite catalyst, $WO_3/SiO_2/Fe_3O_4$ At ambient temperature, 17.7 g of ammonium metatungstate and 10 mL of deionized water were added sequentially into a 50 mL beaker, the mixture was continuously stirred until completely dissolved, the $SiO_2/Fe_3O_4$ composite nano-particles prepared in step 2) were then added and stirring was continued vigorously for 12 hours. Afterwards, the beaker was placed in an oven at 110° C. for 12 hours for drying. Then, the mixture was ground in a mortar and passed through a 120-mesh standard sieve. The obtained solid powder was placed in a muffle furnace and calcined at 550° C. for 3 hours to obtain the magnetic separable core-shell supported tungsten composite catalyst, $WO_3/SiO_2/Fe_3O_4$, for use.

Except that the molar ratios of ammonium metatungstate:TEOS:$FeCl_3$ used were listed in Table 1, the other implementation steps and implementation conditions were the same in Examples 1-12.

TABLE 1

The molar ratios of ammonium metatungstate:TEOS:$FeCl_3$ used in Examples 1-12

| No. | The molar ratio of ammonium metatungstate:TEOS:$FeCl_3$ |
|---|---|
| Example 1 | 1:10:2.5 |
| Example 2 | 1:10:5 |
| Example 3 | 1:10:7.5 |
| Example 4 | 1:10:10 |
| Example 5 | 1:15:10 |
| Example 6 | 1:30:10 |
| Example 7 | 1:40:10 |
| Example 8 | 1:50:10 |
| Example 9 | 1:60:10 |
| Example 10 | 1:70:10 |
| Example 11 | 1:80:10 |
| Example 12 | 1:90:10 |

Examples a1-a12: the Preparation Method of Quinolone Compounds 24.6 g of ethyl formylacetate sodium salt, 100 mL of toluene and 4 g of $WO_3/SiO_2/Fe_3O_4$ catalyst were charged into a reactor, 8.7 g of dimethylamine was introduced with stirring, 10 g of 2,4-dichloro-5-fluorobenzoyl chloride was added, and the reaction was carried out at a certain temperature for 1 hour. Cyclopropanamine was added dropwise at 50° C., and $CO_2$ was introduced at the same time to control the reaction pressure at 1.5-2 atmospheres. After the reaction was carried out for 1 hour, 12 g of flake caustic soda and 200 mL of toluene were added into the reaction solution, the reaction solution was stirred, and the temperature was raised to 100° C. for half an hour. The catalyst was recovered by filtration, and toluene was recovered to dryness by increasing the pressure. An appropriate amount of water was added, and the temperature was raised to 100° C. After the system was clear, hydrochloric acid was added dropwise to adjust the power of hydrogen. After being precipitated, the crystals were centrifuged and dried to obtain the organic amine of formula (V).

The sources of the catalyst $WO_3/SiO_2/Fe_3O_4$ used in Examples a1-a12 were listed in Table 2, and the other implementation steps and implementation conditions were the same.

TABLE 2

The conditions and yields for each of Examples a1-a12

| No | The source of the catalyst $WO_3/SiO_2/Fe_3O_4$ used | The dosage of the catalyst mass ratio (catalyst:ethyl formylacetate sodium salt) | The power of hydrogen adjusted with hydrochloric acid pH value | The cyclization time (h) | The yield of the organic amine of formula (V) (%) |
|---|---|---|---|---|---|
| Example a1 | Example 1 | 1:5 | 5 | 0.5 | 49.5 |
| Example a2 | Example 2 | 1:5 | 5 | 0.5 | 50.1 |
| Example a3 | Example 3 | 1:5 | 5 | 0.5 | 63.2 |
| Example a4 | Example 4 | 1:5 | 5 | 0.5 | 65.0 |
| Example a5 | Example 5 | 1:5 | 5 | 0.5 | 68.1 |
| Example a6 | Example 6 | 1:5 | 5 | 0.5 | 67.5 |
| Example a7 | Example 7 | 1:5 | 5 | 0.5 | 66.1 |
| Example a8 | Example 8 | 1:5 | 5 | 0.5 | 55.2 |
| Example a9 | Example 9 | 1:10 | 5 | 0.5 | 70.6 |
| Example a10 | Example 10 | 1:20 | 5 | 0.5 | 69.4 |
| Example a11 | Example 11 | 1:10 | 4 | 0.5 | 75.9 |
| Example a12 | Example 12 | 1:10 | 4 | 1 | 79.5 |

Taking Example a12 as an example, the yield of the organic amine of formula (V) with the catalyst from Example 12 can be 79.5% under this condition. In addition, under this catalytic condition, the magnetic separable core-shell supported tungsten composite catalyst, $WO_3/SiO_2/Fe_3O_4$, still retained an excellent yield of the organic amine of formula (V) with no significant decrease in the catalytic effect when the catalyst from Example 12 was recovered and recycled for five times. See Table 3 below for details:

TABLE 3

The recycle experiments of the magnetic separable core-shell supported tungsten composite catalyst, $WO_3/SiO_2/Fe_3O_4$

| No | The cycle number of the catalyst | The yield of the organic amine of formula (V) (%) | The recovery rate of the catalyst (%) |
|---|---|---|---|
| 1 | Example a12, the first time | 79.5 | 98.1 |
| 2 | Example a12, the second time | 78.9 | 97.2 |
| 3 | Example a12, the third time | 78.2 | 97.5 |
| 4 | Example a12, the fourth time | 77.4 | 96.2 |
| 5 | Example a12, the fifth time | 76.5 | 95.7 |

The examples listed above are just a few specific examples of the present invention. Obviously, the present invention is not limited to the above examples, and many variations are possible. All the variations that can be directly derived or be conceivable by those of ordinary skills in the art from the disclosure of the present invention shall be considered to fall within the protection scope of the present invention.

The invention claimed is:

1. A preparation method of a core-shell structure supported tungsten composite catalyst, comprising the steps of:
    step 1), adding a reducing agent and a base into an aqueous solution of iron compound, heating to 50-80° C. and stirring to obtain $Fe_3O_4$ colloid;
    step 2), adding the $Fe_3O_4$ colloid obtained in the step 1), tetraethyl orthosilicate and a hydrolysis catalyst into an appropriate amount of dispersion solvent and allowing to react for 4-8 hours to obtain $SiO_2/Fe_3O_4$ composite nano-particles; and
    step 3), adding the $SiO_2/Fe_3O_4$ composite nano-particles obtained in step 2) into an aqueous solution of ammonium metatungstate, stirring for 8-14 hours and drying at 90-150° C. to obtain a first solid, which is calcined at 450-650° C. for 1-6 hours to obtain a magnetic separable core-shell structure supported tungsten composite catalyst, $WO_3/SiO_2/Fe_3O_4$;
    wherein the molar ratio of the iron compound: tetraethyl orthosilicate:ammonium metatungstate=1:1-10:0.1-1;
    and wherein the iron compound is $FeCl_3$, $FeCl_3 \cdot 6H_2O$ or ferric triacetylacetonate; the reducing agent is $Na_2SO_3$, ascorbic acid or hydrazine hydrate; and the base is aqueous ammonia, sodium hydroxide or sodium acetate.

2. The preparation method according to claim 1, wherein the iron compound is $FeCl_3$.

3. The preparation method according to claim 1, wherein the reducing agent is $Na_2SO_3$.

4. The preparation method according to claim 1, wherein the base is aqueous ammonia.

5. The preparation method according to claim 1, wherein in step 1), after heating, polyvinylpyrrolidone is added as a surfactant, the mixture is stirred continuously, then centrifuged and washed with water, and finally dispersed, and water is then removed to obtain $Fe_3O_4$ colloid.

6. The preparation method according to claim 1, wherein in step 2), the dispersion solvent is ethanol, and the hydrolysis catalyst is aqueous ammonia.

7. The preparation method according to claim 1, wherein in step 3), the first solid is first ground through a 120-mesh standard sieve and then calcined at 450-650° C. for 1-6 hours.

8. A magnetic separable core-shell supported tungsten composite catalyst, $WO_3/SiO_2/Fe_3O_4$, prepared by the preparation method of claim 1.

9. A magnetic separable core-shell supported tungsten composite catalyst, $WO_3/SiO_2/Fe_3O_4$, prepared by the preparation method of claim 2.

10. A magnetic separable core-shell supported tungsten composite catalyst, $WO_3/SiO_2/Fe_3O_4$, prepared by the preparation method of claim 3.

11. A magnetic separable core-shell supported tungsten composite catalyst, $WO_3/SiO_2/Fe_3O_4$, prepared by the preparation method of claim 4.

12. Use of the magnetic separable core-shell structure supported tungsten composite catalyst, $WO_3/SiO_2/Fe_3O_4$, of claim 8 in the synthesis of quinolone compounds, wherein the reaction steps are as follows:
    step 1), stirring and mixing ethyl formylacetate sodium salt, a non-polar organic solvent and the $WO_3/SiO_2/Fe_3O_4$ catalyst, introducing an amine compound, adding 2,4-dichloro-5-fluorobenzoyl chloride and allowing to react for 0.5-3 hours;
    step 2), following step 1), adding a primary amine dropwise while introducing $CO_2$ to control the reaction pressure at 1-5 atmospheres and allowing to react for 0.5-3 hours;
    step 3), following step 2), adding an alkali metal hydroxide and a non-polar organic solvent, stirring and raising the temperature to 100° C. for half an hour, filtering to recover the catalyst and increasing the pressure to recover the non-polar organic solvent; and
    step 4), following step 3), adding an appropriate amount of water, raising the temperature to 100° C., adding hydrochloric acid dropwise to adjust the power of hydrogen to control the pH range at 4.8-6.5, precipitating crystals, followed by centrifugation and drying, and obtaining quinolone compounds;
    wherein the non-polar organic solvent is toluene, xylene or a mixture of the former two; the amine compound is dimethylamine, diethylamine or dicyclohexylamine; the primary amine is cyclopropylamine or S-propylene glycol amine; and the alkali metal hydroxide is sodium hydroxide, lithium hydroxide or potassium hydroxide.

13. Use of the magnetic separable core-shell structure supported tungsten composite catalyst, $WO_3/SiO_2/Fe_3O_4$, of claim 9 in the synthesis of quinolone compounds, wherein the reaction steps are as follows:
    step 1), stirring and mixing ethyl formylacetate sodium salt, a non-polar organic solvent and the $WO_3/SiO_2/Fe_3O_4$ catalyst, introducing an amine compound, adding 2,4-dichloro-5-fluorobenzoyl chloride and allowing to react for 0.5-3 hours;
    step 2), following step 1), adding a primary amine dropwise while introducing $CO_2$ to control the reaction pressure at 1-5 atmospheres and allowing to react for 0.5-3 hours;

step 3), following step 2), adding an alkali metal hydroxide and a non-polar organic solvent, stirring and raising the temperature to 100° C. for half an hour, filtering to recover the catalyst and increasing the pressure to recover the non-polar organic solvent; and step 4), following step 3), adding an appropriate amount of water, raising the temperature to 100° C., adding hydrochloric acid dropwise to adjust the power of hydrogen to control the pH range at 4.8-6.5, precipitating crystals, followed by centrifugation and drying, and obtaining quinolone compounds;

wherein the non-polar organic solvent is toluene, xylene or a mixture of the former two; the amine compound is dimethylamine, diethylamine or dicyclohexylamine; the primary amine is cyclopropylamine or S-propylene glycol amine; and the alkali metal hydroxide is sodium hydroxide, lithium hydroxide or potassium hydroxide.

14. Use of the magnetic separable core-shell structure supported tungsten composite catalyst, $WO_3/SiO_2/Fe_3O_4$, of claim 10 in the synthesis of quinolone compounds, wherein the reaction steps are as follows:

step 1), stirring and mixing ethyl formylacetate sodium salt, a non-polar organic solvent and the $WO_3/SiO_2/Fe_3O_4$ catalyst, introducing an amine compound, adding 2,4-dichloro-5-fluorobenzoyl chloride and allowing to react for 0.5-3 hours;

step 2), following step 1), adding a primary amine dropwise while introducing $CO_2$ to control the reaction pressure at 1-5 atmospheres and allowing to react for 0.5-3 hours;

step 3), following step 2), adding an alkali metal hydroxide and a non-polar organic solvent, stirring and raising the temperature to 100° C. for half an hour, filtering to recover the catalyst and increasing the pressure to recover the non-polar organic solvent; and step 4), following step 3), adding an appropriate amount of water, raising the temperature to 100° C., adding hydrochloric acid dropwise to adjust the power of hydrogen to control the pH range at 4.8-6.5, precipitating crystals, followed by centrifugation and drying, and obtaining quinolone compounds;

wherein the non-polar organic solvent is toluene, xylene or a mixture of the former two; the amine compound is dimethylamine, diethylamine or dicyclohexylamine; the primary amine is cyclopropylamine or S-propylene glycol amine; and the alkali metal hydroxide is sodium hydroxide, lithium hydroxide or potassium hydroxide.

15. Use of the magnetic separable core-shell structure supported tungsten composite catalyst, $WO_3/SiO_2/Fe_3O_4$, of claim 11 in the synthesis of quinolone compounds, wherein the reaction steps are as follows:

step 1), stirring and mixing ethyl formylacetate sodium salt, a non-polar organic solvent and the $WO_3/SiO_2/Fe_3O_4$ catalyst, introducing an amine compound, adding 2,4-dichloro-5-fluorobenzoyl chloride and allowing to react for 0.5-3 hours;

step 2), following step 1), adding a primary amine dropwise while introducing $CO_2$ to control the reaction pressure at 1-5 atmospheres and allowing to react for 0.5-3 hours;

step 3), following step 2), adding an alkali metal hydroxide and a non-polar organic solvent, stirring and raising the temperature to 100° C. for half an hour, filtering to recover the catalyst and increasing the pressure to recover the non-polar organic solvent; and step 4), following step 3), adding an appropriate amount of water, raising the temperature to 100° C., adding hydrochloric acid dropwise to adjust the power of hydrogen to control the pH range at 4.8-6.5, precipitating crystals, followed by centrifugation and drying, and obtaining quinolone compounds;

wherein the non-polar organic solvent is toluene, xylene or a mixture of the former two; the amine compound is dimethylamine, diethylamine or dicyclohexylamine; the primary amine is cyclopropylamine or S-propylene glycol amine; and the alkali metal hydroxide is sodium hydroxide, lithium hydroxide or potassium hydroxide.

16. The use according to claim 12, wherein the non-polar organic solvent is toluene, the amine compound is dimethylamine, the primary amine is cyclopropylamine, and the alkali metal hydroxide is sodium hydroxide.

17. The use according to claim 13, wherein the non-polar organic solvent is toluene, the amine compound is dimethylamine, the primary amine is cyclopropylamine, and the alkali metal hydroxide is sodium hydroxide.

18. The use according to claim 14, wherein the non-polar organic solvent is toluene, the amine compound is dimethylamine, the primary amine is cyclopropylamine, and the alkali metal hydroxide is sodium hydroxide.

19. The use according to claim 15, wherein the non-polar organic solvent is toluene, the amine compound is dimethylamine, the primary amine is cyclopropylamine, and the alkali metal hydroxide is sodium hydroxide.

* * * * *